(12) United States Patent
Chang et al.

(10) Patent No.: US 8,877,260 B2
(45) Date of Patent: Nov. 4, 2014

(54) USE OF ACACIA EXTRACTS AND THEIR COMPOUNDS ON INHIBITION OF XANTHINE OXIDASE

(71) Applicant: National Taiwan University, Taipei (TW)

(72) Inventors: Shang-Tzen Chang, Taipei (TW); Yu-Tang Tung, Taichung (TW)

(73) Assignee: National Taiwan University, Taipei (TW)

( * ) Notice: Subject to any disclaimer, the term of this patent is extended or adjusted under 35 U.S.C. 154(b) by 93 days.

(21) Appl. No.: 13/793,875

(22) Filed: Mar. 11, 2013

(65) Prior Publication Data
US 2013/0189383 A1    Jul. 25, 2013

Related U.S. Application Data

(60) Division of application No. 13/233,284, filed on Sep. 15, 2011, now Pat. No. 8,414,936, which is a continuation-in-part of application No. 12/534,708, filed on Aug. 3, 2009, now abandoned.

(30) Foreign Application Priority Data

Jun. 8, 2009 (TW) ................. 98119117 A (51) Int. Cl.
*A01N 65/00* (2009.01)
*A61K 31/12* (2006.01)
*A23L 1/03* (2006.01)
*A61K 45/06* (2006.01)
*A23C 20/02* (2006.01)
*A23L 1/30* (2006.01)
*A61K 31/352* (2006.01)
*A61K 36/48* (2006.01)

(52) U.S. Cl.
CPC ............... *A61K 36/48* (2013.01); *A61K 31/12* (2013.01); *A23L 1/031* (2013.01); *A61K 45/06* (2013.01); *A23C 20/025* (2013.01); *A23L 1/3002* (2013.01); *A61K 31/352* (2013.01); *A23V 2002/00* (2013.01)
USPC ........................................... 424/725

(58) Field of Classification Search
None
See application file for complete search history.

(56) References Cited

FOREIGN PATENT DOCUMENTS

JP    2003095773 A   *   4/2003

* cited by examiner

*Primary Examiner* — Michael Meller
(74) *Attorney, Agent, or Firm* — WPAT, P.C.; Anthony King (57) ABSTRACT

The present invention relates to a method for inhibition of xanthine oxidase comprising administrating an effective amount of the extracts from *Acacia* spp.

1 Claim, 7 Drawing Sheets

USE OF ACACIA EXTRACTS AND THEIR COMPOUNDS ON INHIBITION OF XANTHINE OXIDASE

CROSS-REFERENCE TO RELATED APPLICATIONS

This application is a divisional application of the pending U.S. patent application Ser. No. 13/233,284 filed on Sep. 15, 2011, which is a Continuation-in-part of the pending U.S. patent application Ser. No. 12/534,708 filed on Aug. 3, 2009, for which priority is claimed and is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention is related to a method for inhibition of xanthine oxidase, comprising administrating an effective amount of *Acacia* extracts.

BACKGROUND OF THE INVENTION

Food derived or in vivo human purine is metabolized into hypoxanthine and xanthine, which can be further catalyzed by xanthine oxidase (XO) into uric acid. Uric acid is the final metabolized product of purine in human. Abnormal purine metabolism leads to hyperuricemia, then urate crystals accumulation in joint, causing joint deformation and gout formation. Currently, local male above thirty years old has gout as high as 3.3%. People in their thirties have the highest tendency of getting gout. This phenomenon indicates that fast economic growth enables our citizen to take more animal protein and high calorie food, which generate more young obese population, and lead to high uric acid population increasing dramatically.

Symptoms of gout caused by high uric acid include muscle spasm, local swelling, inflammation, joint pain, muscle fatigue, sense of pressure and myocardial infarction. There are several commercially available medicines for treating gout, such as benzbromarone (URINORM), probenecid, allopurinol, bucolome, cinchophan, and colchicine, wherein allopurinol is a commonly used drug in clinic. Functions of these drugs are inhibiting uric acid formation, removing extra uric acid in vivo, working in kidney to help reduce uric acid, inhibiting xanthine oxidase activity which is responsible for metabolizing xanthine into uric acid, and accelerating in vivo uric acid secretion. However, these uric acid excretion promoting drugs have certain side effects, such as urolithiasis, GI disturbance, jaundice, kidney overloading, allergy and anemia. Therefore, despite lots of available drugs for gout treatment, there is still need for new drug or food additive to reduce uric acid content and to treat gout as well as gout related symptoms.

Xanthine oxidase not only metabolizes xanthine into uric acid in vivo, but also generates superoxide radical ($O_2^{\bullet-}$) and peroxide ($H_2O_2$) in the reaction. The biochemical reactions are shown below:

Due to the instability of free radical, it is extremely easy to react with cells and tissues in vivo, and the reaction is summed as oxidation which may lead to cell malfunction. For example, if the oxidation occurs on the lipid of cell membrane, it can change cell membrane permeability, and cell necrosis is observed when nutrient and metabolite are unable to pass through cell. If cell membrane damage rate is faster than cell regeneration rate, tissue function will be affected significantly. If the oxidation attacks protein, it will lead to protein losing normal physiological function and cause diseases. For example, if oxidation occurs in subcutaneous collagen tissue, it may cause aging by losing skin elasticity and hydration. Besides, free radical will destroy DNA, causing DNA breakage or base mutation. Once DNA is broken, it may repair abnormally and lead to mutation during human repair process. Base pair attacked by free radicals will generate some by-products which may cause genetic error and possibility of carcinogenesis. If human suffers long term serial damages as described above, all kinds of chronic diseases, aging, and cancer may come along.

*Acacia* belongs to Leguminosae, is a commonly seen plant in low altitude and hills. Currently, the main function of *Acacia* is for traditional fuel wood and for structural wood. Besides,*Acacia* is one of the allelopathic species. The compounds of *Acacia confusa* leave possess bioactivity proven in sea shrimp lethal test. Some researches found that *Acacia* extracts contains flavonoid (Lai Yeap Foo, Phytochemistry, Vol. 26, No. 3, pp.813-817 (1987); Elfranco Malan, Phytochemistry, Vol. 33, No. 3, pp. 733-734 (1993); Wu et al., Journal of Agricultural and Food Chemistry, Vol. 56, No. 5, pp. 1567-1573 (2008); Lee et al., Journal of Natural Products, Vol. 63, No. 5, pp. 710-712 (2000); Tung et al., Food Chemistry, Vol. 115, No. 3, pp. 1019-1024 (2009); Wu et al., Journal of Agricultural and Food Chemistry, Vol. 56, No. 2, pp. 328-332 (2008); Lee et al., Bot. stud, Vol. 47, pp. 37-43 (2006) and Wu et al., Journal of Agricultural and Food Chemistry, Vol. 53, No. 2, pp. 5917-5921 (2005)). However, xanthine oxidase inhibition compounds from *Acacia* bark, heartwood, even leaves have not been discovered to date.

SUMMARY OF THE INVENTION

The present invention provides a composition for inhibition of xanthine oxidase, comprising administrating an effective amount of *Acacia* extracts.

DETAILED DESCRIPTION OF THE INVENTION

The present invention provides a composition for inhibition of xanthine oxidase, comprising an effective amount of *Acacia* alcoholic extracts and a pharmaceutically acceptable carrier. This composition is used to reduce individual's uric acid and free radical production. This compound is an effective component extracted from *Acacia* by organic solvent, such as ethanol or water.

The present invention also provides a method for inhibition of xanthine oxidase in a subject in need, comprising administrating the subject an effective amount of an alcoholic extract of *Acacia*. This method is used to reduce subject's uric acid concentration and inhibit free radical production induced by xanthine oxidase in vivo.

The alcoholic extract of *Acacia* in present invention is extracted from *Acacia* heartwood, bark, branches, flowers, twigs, roots and leaves. Extracts with preferred xanthine oxidase inhibitory activity is extracted from heartwood, and the second preferred one is extracted from bark.

The *Acacia* extract by organic solvent, such as ethanol, of the present invention is further separated in liquid-liquid fraction with ethyl acetate, n-butyl alcohol and water to generate ethyl acetate fraction, n-butyl alcohol fraction and water fraction. The ethyl acetate fraction with better xanthine oxidase inhibitory activity can isolate eight major compounds, including 3,7,8,3',4'-pentahydroxyflavone (Melanoxetin), 7,8,3',4'-tetrahydroxyflavon, 3,4,2',3',4'-pentahydroxy trans-chalcone (Okanin), 7,8,3',4'-tetrahydroxy-3-methoxyflavone (Transilitin), 3,7,8,3'-tetrahydroxy-4'-methoxyflavone, 7,8,3'-trihydroxy-3,4'-dimethoxyflavone, 7,3',4'-trihydroxyflavone and 7,3',4'-trihydroxy-3-methoxyflavone, wherein the substances with better xanthine oxidase inhibitory activity are melanoxetin and okanin, and the best one is okanin. The xanthine oxidase inhibitory activity of melanoxetin and okanin is 17 fold and 63 fold higher than current gout treating drug allopurinol. Therefore, they are potential substitutes for allopurinol which has side effect.

The *Acacia* of the present invention includes but is not limited to *Acacia acinacea, Acacia albida, Acacia aneura, Acacia Arabica, Acacia auriculiformis, Acacia baileyana, Acacia baileyana, Acacia bealbat, Acacia binervia, Acacia brachybotrya, Acacia bussei, Acacia bynoeana, Acacia caesia, Acacia calamifolia, Acacia cardiophylla, Acacia catechu, Acacia cavenia, Acacia concinna, Acacia confusa, Acacia cornigera, Acacia cultriformis, Acacia cultriformis, Acacia cyanophylla, Acacia cyclopis, Acacia dealbara, Acacia decora, Acacia decurrens, Acacia elongate, Acacia falcate, Acacia farnesiana, Acacia fimbriata, Acacia giraffae, Acacia gregii, Acacia gummifera, Acacia holosericea, Acacia homalophylla, Acacia horrida, Acacia howittii, Acacia implexa, Acacia juniperina, Acacia karroo, Acacia kettlewelliae, Acacia koa, Acacia lenticularis, Acacia leprosa, Acacia leucophloea, Acacia longifolia, Acacia mangium, Acacia mearnsii, Acacia melanoxylon, Acacia mellifera, Acacia merrillii, Acacia mollissima, Acacia nigrescens, Acacia nilotica, Acacia paniculata, Acacia paradoxa, Acacia pendula, Acacia pennata, Acacia penninervis, Acacia podalyriifolia, Acacia pravissima, Acacia prominens, Acacia pruinosa, Acacia pubescens, Acacia pycnantha, Acacia retinodes, Acacia richii, Acacia rigens, Acacia rubida, Acacia salicina, Acacia Senegal, Acacia seyal, Acacia sinuate, Acacia spectabilis, Acacia spirocarpa, Acacia suaveolens, Acacia terminalis, Acacia vestita, Acacia victoriae, Acacia woodii*, wherein the preferable *Acacia* is *Acacia melanoxylon, Acacia nigrescens* or *Acacia confusa*, and the most preferred is *Acacia confusa*.

The alcoholic extract of *Acacia* in the present invention is used as drug, health food or food additives that gout patient can't take too much such as tofu or other related soybean products, to treat gout caused by uric acid generated by xanthine oxidase or to improve high uric acid related symptoms such as muscle spasm, local swelling, inflammation, joint pain, muscle fatigue, sense of pressure and myocardial infarction. The *Acacia* extracts of the present invention are used as food additives that are added into tofu or other related soybean products.

There are publications regarding *Acacia* extracts on free radical inhibition and antioxidant (Chang et al., Journal of Agricultural and Food Chemistry, Vol. 49, pp. 3420-3424 (2001); Wu et al., Journal of Agricultural and Food Chemistry, Vol.53, pp. 5917-5921 (2005); Wu et al., Journal of Agricultural and Food Chemistry, Vol. 56, No. 5, pp. 1567-1573 (2008); Lee et al., Bot. Stud., Vol. 47, pp. 37-43 (2006); Tung et al., Food Chemistry, Vol. 115, No. 3, pp. 1019-1024 (2009); Wu et al., Journal of Agricultural and Food Chemistry, Vol. 56, No. 2, pp. 328-332 (2008); Tung et al., Bioresource Technology, Vol. 100, No. 1, pp. 509-514 (2009); and Tung et al., Bioresource Technology, Vol. 98, No. 5, pp. 1120-1123 (2007)). However, there is no research showing that *Acacia* extracts can inhibit free radical generated by xanthine oxidase in vivo. The alcoholic extract of *Acacia* in the present invention is used as drug, health food, or cosmetics for inhibiting free radicals generated by xanthine oxidase in vivo, and improve free radical induced diseases. For example, 1: cell membrane damage causes cell unable to absorb nutrient and leads to dermatitis, acne, skin pigmentation, age spot and wound healing problem; 2: attacked collagen and elastin cause skin aging, wrinkle and dull skin; 3: destroyed immune system leads to low immunogenicity, easy to catch cold, airway damage, lupus and psoriasis; 4: promoting lipid peroxide formation, causes arterioles fibrosis, atherosclerosis, hypertension, cardiovascular related diseases, cerebral hemorrhage and stroke; 5: promoting lipid accumulation in organs or other connective tissues and causes hepatitis, fatty liver, liver cirrhosis, pancreatitis, gastritis, constipation, nephritis, acute renal failure, diabetes, red eyes, retinopathy, cataracts, Alzheimer's disease, Parkinson's disease and memory impairment; 6: DNA and RNA damage causes chromosome change and cell mutation derived tumor and cancer.

The composition of present invention further includes oligo peptide, free amino acid, carnitine and pharmaceutically or physiologically acceptable recipient to form medical composition. The preferred pharmaceutically acceptable recipient includes but is not limited to dextrin, lactose, starch, soapstone, stearic acid, tartaric acid, ethanol, glycerol, vegetable oil and wax.

If apply the present invention as a drug, the composition of the present invention can be prepared by known method in appropriate medical formulation with appropriate pharmaceutically acceptable recipient, such as tablet, powder, granule, capsule, liquid or suspension (via different route of administration). The composition of the present invention can be administrated through any route, such as oral or parental route to reduce individual's uric acid such as mammalian animal, preferred in human. In other words, the composition of the present invention can be used to control uric acid content of individual gout patient, to improve high uric acid or free radical related symptoms such as muscle spasm, local swelling, inflammation, joint pain, muscle fatigue, sense of pressure and myocardial infarction.

If apply the present invention as food additives, the composition of the present invention can be used by known method in appropriate formulation for oral administration, such as tablet, powder, granule, capsule, liquid and suspension, or topical formulation such as caplet, small particle, stick, thread, fumigant or pill. Oral formulation can be further applied in health food, and topical formulation can be applied in facial mask, toner, serum, lotion or cosmetics.

Lots of uric acid excretion promoting drugs for gout treatment is commercially available, such as benzbromarone (URINORM), probenecid, allopurinol, bucolome, cinchophan and colchicine. The composition of the present invention can combine with one or more uric acid excretion promoting drug as described above to reduce uric acid. With combination application, the composition of the present invention and one or more uric acid excretion promoting drug can be administered in sequence or simultaneously. For example, the composition of the present invention can be used in single formulation, further containing one or more uric acid excretion promoting drug. The composition of the present invention can also be used in separate formulation with one ore more uric acid excretion promoting drug, and administered or applied simultaneously or in sequence.

The pharmaceutically acceptable carrier of the present invention can be used via oral, under the tongue, rectum, nasal cavity, virgina, abdominal cavity, inside the cancer, inside joint, inside eye ball, surface of eye ball, epidermis, skin and other possible application method such as injection, patch and so on. Formulation can be unit formulation and prepared by traditional formulation technology which includes mixing active ingredient with medical vector or excipient.

EXAMPLE

Following examples are used as references to clarify the present invention. Examples are only used for description purpose and not the limitation of the present invention.

Example 1

Xanthine Oxidase Inhibitory Activity of Ethanolic Extracts from Various Parts of *Acacia confusa*

Various parts of *Acacia confusa* were cold extracted by ethanol for 3 times, 7 days for each time. The extraction solution was vacuum filtered with Whatman#1 filter paper to remove impurities. The filtered extraction solution was concentrated by rotatory vacuum evaporator and lyophilized by a lyophilizer for xanthine oxidase inhibition assay. This assay was detecting xanthine derived uric acid, which was catalyzed by xanthine oxidase, at specific absorbance of UV 295 nm Therefore, 2 µL of various concentrations of sample were mixed with 798 µL of sodium pyrophosphate buffer (pH 7.5) and 0.1 U of xanthine oxidase for 5 min at 37° C. 200 µL of 0.6 mM xanthine were added and vortex to mix thoroughly, and measured OD 295 nm absorbance by UV/visible light spectrophotometer. Finally, xanthine oxidase inhibitory rate of extracts (%) was calculated.

$$\text{Inhibitory rate of xanthine oxidase (\%)} = \left(1 - \frac{\text{Reaction rate of experimental group}}{\text{Reaction rate of control}}\right) \times 100$$

Figure 1:
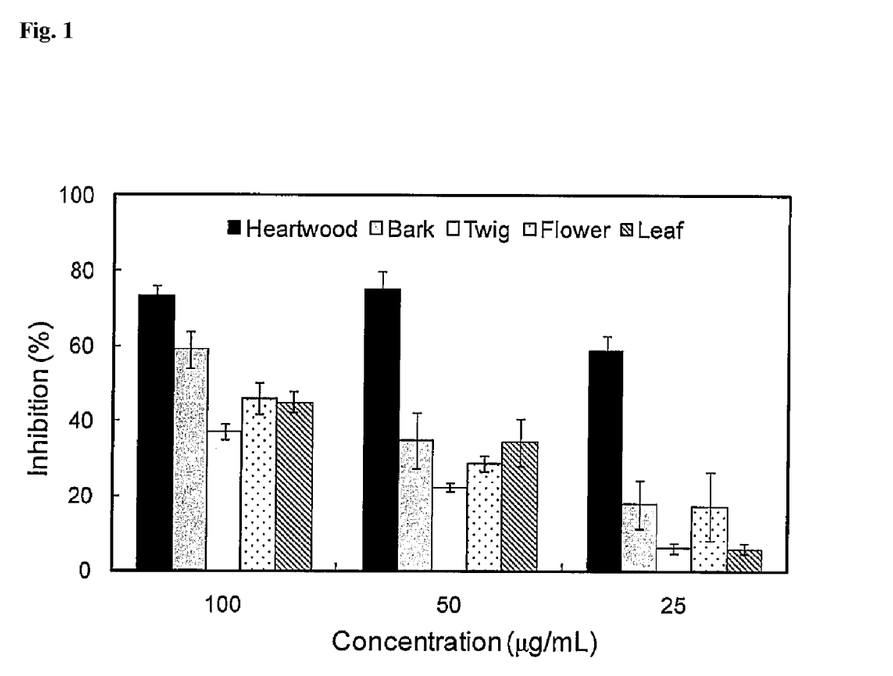
FIG. 1. Xanthine oxidase inhibitory activity of ethanolic extracts from various parts of *Acacia confusa*.

FIG. 1 showed xanthine oxidase inhibitory activity of ethanolic extracts from various parts of *Acacia confusa*. The inhibition rate was increased along with the elevated ethanolic extracts concentration Inhibition rate of various parts were compared, heartwood extract showed the most significant effect with $EC_{50}$ of 11.7 µg/mL, and the second one was bark extract.

Example 2

Xanthine Oxidase Inhibitory Activity of *Acacia confusa* Heartwood Extracts and their Solubles Ethanolic extract from *Acacia confusa* heartwood was applied in liquid-liquid partition with solvents of various polarities, such as ethyl acetate, n-butyl alcohol and water, to further separate *Acacia confusa* heartwood ethanolic extract into ethyl acetate fraction, n-butyl alcohol fraction and water fraction for inhibition assay of xanthine oxidase as described in Example 1.

Figure 2:
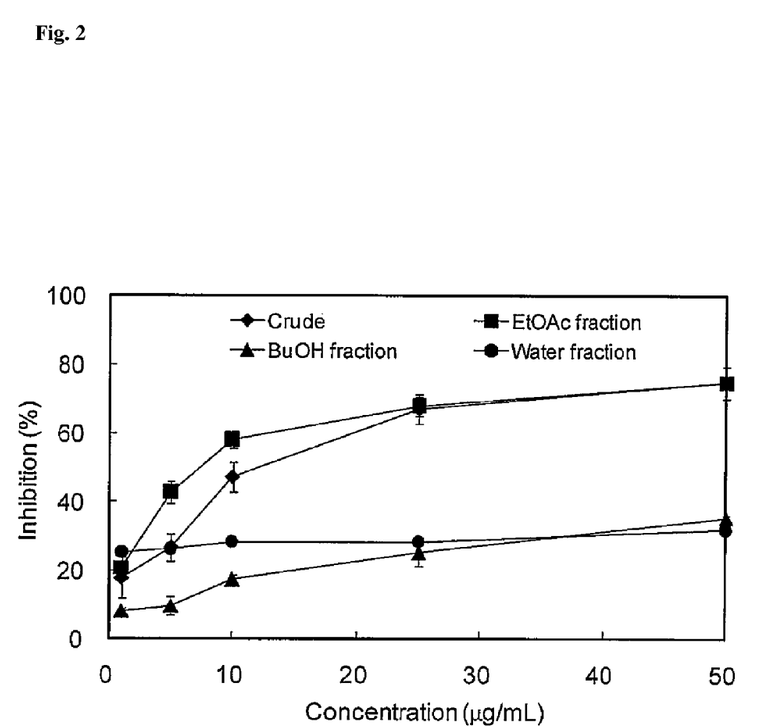
FIG. 2. Xanthine oxidase inhibitory activity of *Acacia confusa* heartwood ethanolic extracts and their solubles.

Inhibitory activity of each solubles from heartwood extracts on xanthine oxidase was further evaluated. As shown in FIG. 2, ethyl acetate fraction had the best effect with $EC_{50}$ of 7.8 µg/mL and the $EC_{50}$ of clinically known xanthine oxidase inhibitory drug—allopurinol—was 1.2 µg/mL.

Example 3

Xanthine Oxidase Inhibitory Activity of Subfraction from *Acacia confusa* Heartwood Chromatography and HPLC, such as RP-18 chromatography, were used to initially separate 50 g of xanthine oxidase inhibiting ethyl acetate solubles. The eluted extracts were grouped as EA1 (elution solvent is 10-20% MeOH/H₂O), EA2-EA3 (30% MeOH/H₂O), EA4 (30-40% MeOH/H₂O), EA5 (40-50% MeOH/H₂O), EA6 (50-60% MeOH/H₂O), EA7 (60% MeOH/H₂O), EA8 (70-80% MeOH/H₂O), EA9 (80-100% MeOH/H₂O) and EA10 (100% THF). The elution solvent and recovery rate were listed in Table 1. EA5 to EA8 had better xanthine oxidase inhibitory activity. When the concentration was 5 µg/mL, the inhibition rate was 74.8 to 80.5%, whereas allopurinol inhibition rate was 78%.

TABLE 1

Elution solvent, recovery rate and xanthine oxidase inhibitory activity of various subfractions of EtoAc fraction from *Acacia confusa* heartwood (at concentration of 5 µg/mL).

| Subtractions | Mobile phase* | Weight (g) | inhibition (%) |
|---|---|---|---|
| EA1 | 10%-20% | 13.9 | 35.9$^d$ |
| EA2 | 30% | 3.1 | 39.4$^d$ |
| EA3 | 30% | 1.7 | 49.4$^c$ |
| EA4 | 30%-40% | 2.4 | 64.1$^b$ |
| EA5 | 40%-50% | 6.1 | 78.7$^a$ |
| EA6 | 50%-60% | 3.3 | 77.8$^a$ |
| EA7 | 60% | 1.1 | 80.5$^a$ |
| EA8 | 70%-80% | 0.9 | 74.8$^a$ |
| EA 9 | 80%-100% | 0.5 | 37.9$^d$ |
| EA10 | THF | 6.4 | 39.3$^d$ |

TABLE 1-continued

Elution solvent, recovery rate and xanthine oxidase inhibitory activity of various subfractions of EtoAc fraction from *Acacia confusa* heartwood (at concentration of 5 μg/mL).

| Subtractions | Mobile phase* | Weight (g) | inhibition (%) |
|---|---|---|---|
| Total weight (g) | | 39.4 | |
| Recovery (%) | | 93.9% | |

*The ratio of MeOH/H$_2$O (v/v).
The inhibition of allopurinol: 78.2%.

Example 4

Xanthine Oxidase Inhibitory Activity of Major Compounds from *Acacia confusa*

Figure 3:
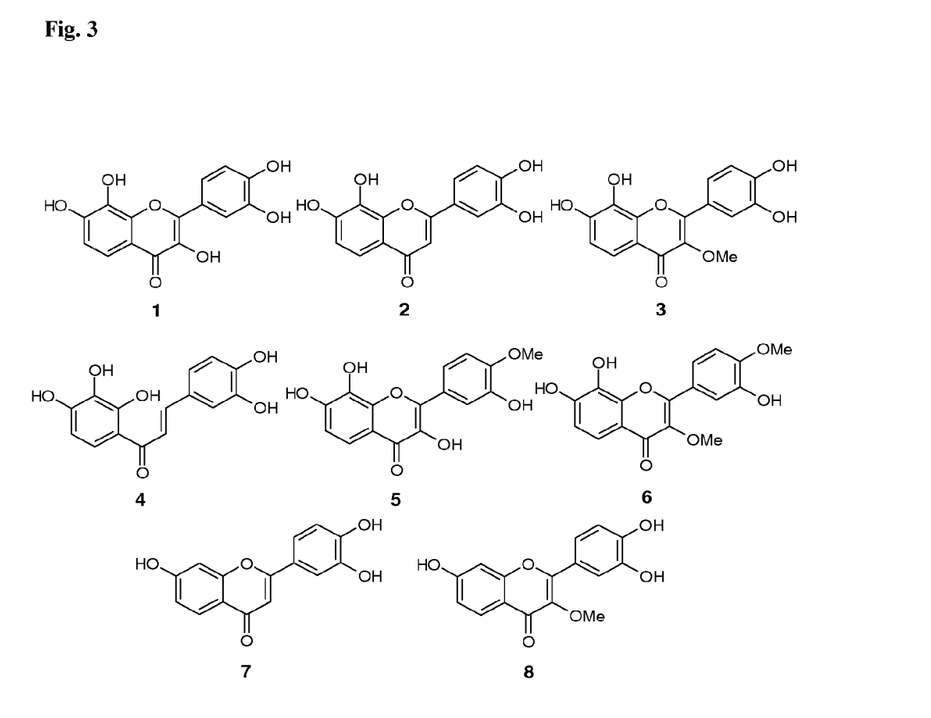
FIG. 3. Major compounds isolated from EtoAc subfraction of *Acacia confusa* heartwood.
Figure 4:
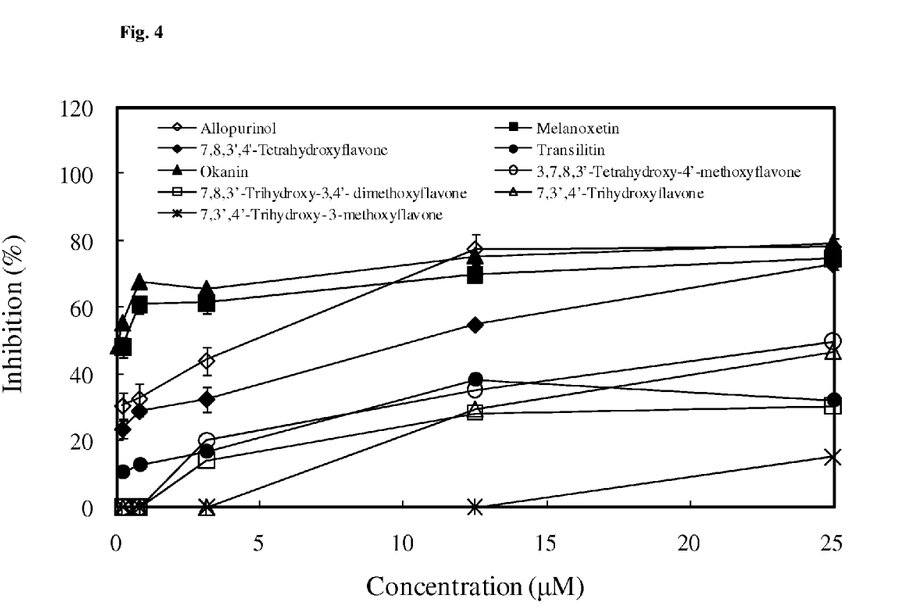
FIG. 4. Xanthine oxidase inhibitory activity of major compounds from *Acacia confusa* heartwood.
Figure 5A:
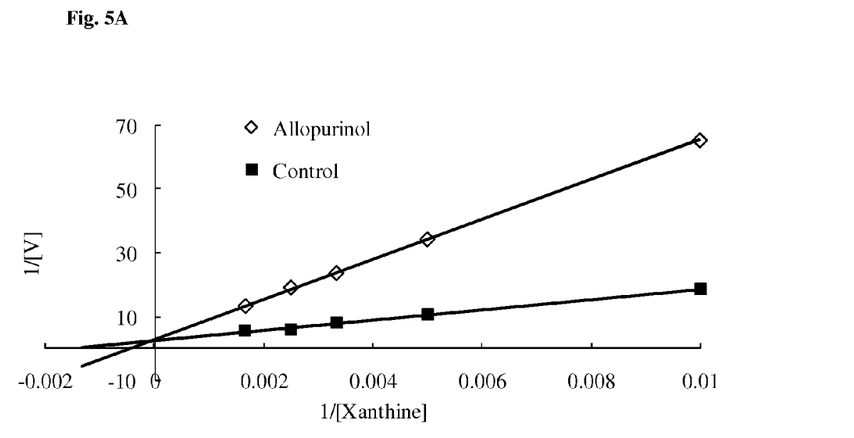
FIG. 5. Kinetic assays of xanthine oxidase inhibition by (A) allopurinol, (B) melanoxetin, (C) 7,8,3',4'-tetrahydroxyflavon and (D) okanin. A Lineweaver-Burk double-reciprocal plot was constructed for the inhibition of xanthine oxidase by (A) allopurinol, (B) melanoxetin, (C) 7,8,3',4'-tetrahydroxyflavon and (D) okanin. The plot is expressed as 1/velocity vs. 1/xanthine ($mM^{-1}$) without or with an inhibitor in the reaction solution.
Figure 5B:
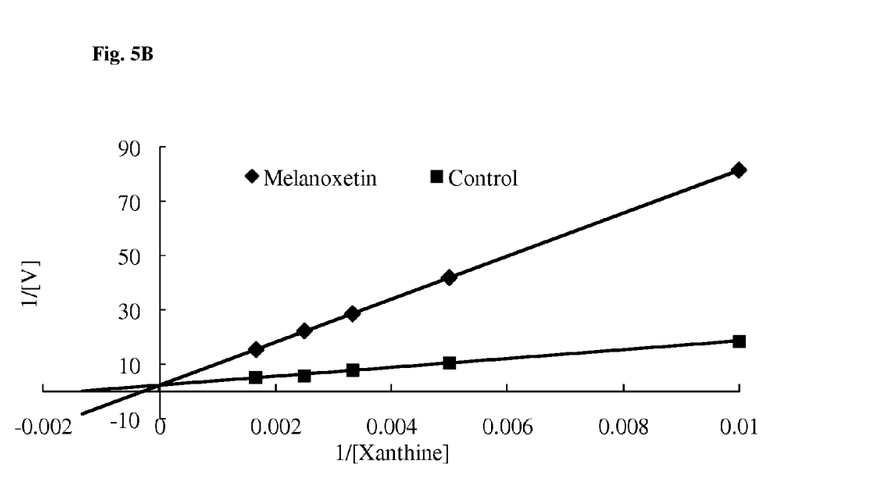
Figure 5C:
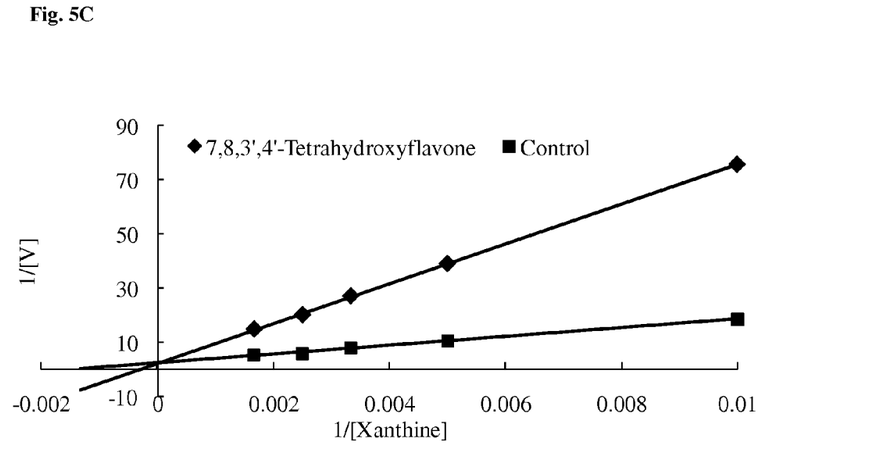
Figure 5D:
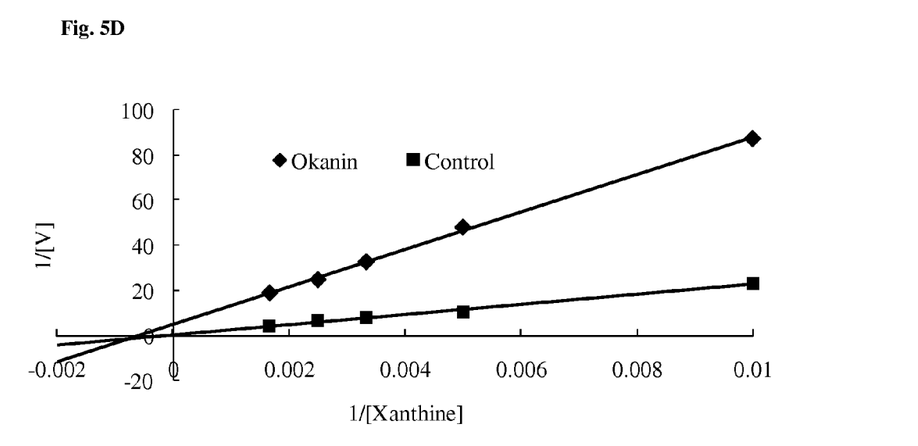

Eight major componunds of EA5 to EA8 subfraction from *Acacia confusa* heartwood were further identified, and their chemical formulas were listed in FIG. 3. These eight major compounds were listed below: 3,7,8,3',4'-pentahydroxyflavone (Melanoxetin), 7,8,3',4'-tetrahydroxyflavon, 7,8,3',4'-tetrahydroxy-3-methoxyflavone (Transilitin), 3,4,2',3',4'-pentahydroxy trans-chalcone (Okanin), 3,7,8,3'-tetrahydroxy-4'-methoxyflavone, 7,8,3'-trihydroxy-3,4'-dimethoxyflavone, 7,3',4'-trihydroxyflavone and 7,3',4'-trihydroxy-3-methoxyflavone. Xanthine oxidase inhibitory assay was performed with these eight compounds, and the results are shown in FIG. 4. It was shown that the EC$_{50}$ of melanoxetin and okanin inhibitory activity on xanthine oxidase was 0.274 μM and 0.074 μM, respectively, and were both better than allopurinol (EC$_{50}$ was 4.784 μM). Therefore, inhibitory activity of melanoxetin and okanin on xanthine oxidase was 17 fold and 63 fold of allopurinol. Melanoxetin and okanin had great potential replacing side-effect possessing allopurinol.

Example 5

Inhibition Mode Determination by Lineweaver-Burk Plot

798 μL of 0.1 unit xanthine oxidase in 200 mM sodium pyrophosphate/sodium chloride buffer (soudium pyrophosphate/HCl, pH 7.5) were mixed with 2 μL of DMSO dissolved melanoxetin, 7,8,3',4'-tetrahydroxyflavon or okanin in 96-well plate at 37° C. for 5 minutes. 0.3, 0.4, or 0.6 mM substrate dissolved in double distilled water were added to start the reaction. OD 295 nm absorbance was detected every one minute by ELISA reader for total eight minutes at ambient temperature. Excel software was used for analyzing the result of enzyme.

FIG. 5 is a Lineweaver-Burk plot showing competitive inhibition mode on xanthine oxidase by melanoxetin and 7,8,3',4'-tetrahydroxyflavon, which was the same as allopurinol. Okanin showed non-competitive inhibition mode with xanthine oxidase substrate.

Example 6

Water Extraction of *Acacia confusa* Heartwood and its Compounds Analysis 1 g of *Acacia confusa* heartwood dry powder was added into 50 mL of water, boiled for 2 hours for hot water extracts, vacuum filtered it on Whatman #1 filter paper, and removed impurity. Hot water extracts was evaporated by rotatory vacuum evaporator for further purify and analyze the major compounds of *Acacia confusa* heartwood hot water extracts.

Figure 6:
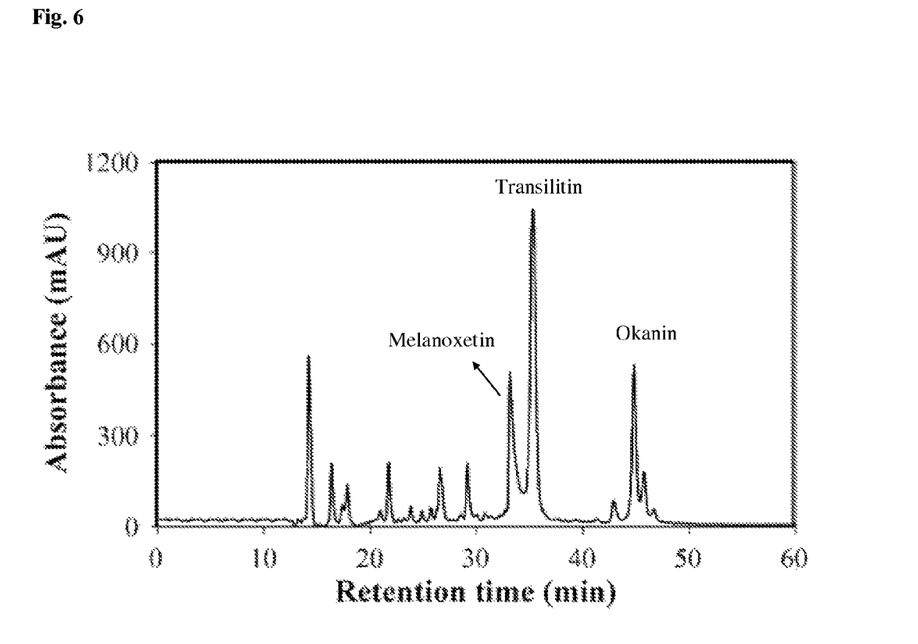
FIG. 6. Fingerprint of *Acacia confusa* heartwood hot water extracts.

As shown in FIG. 6, water extracts contained the same compounds as organic solvent extracts, such as 3,7,8,3',4'-pentahydroxyflavone (Melanoxetin), 7,8,3',4'-tetrahydroxy-3-methoxyflavone (Transilitin), 3,4,2',3',4'-pentahydroxy trans-chalcone (Okanin) for xanthine oxidase inhibition. Therefore, either water extracts or organic solvent extracts of *Acacia confusa* contains xanthine oxidase inhibition compounds.

What is claimed is:
1. A method for treating atherosclerosis, stroke or hypertension consisting essentially of administering to a human in need thereof a therapeutically effective amount of a capsule or tablet of an extract of the heartwood of *Acacia* confusa.

* * * * *